United States Patent [19]

Scheiffele et al.

[11] Patent Number: 5,484,605
[45] Date of Patent: Jan. 16, 1996

[54] AGENT FOR TREATING CHRONICALLY INFLAMMATORY INTESTINAL DISEASES

[75] Inventors: Ekkehard Scheiffele; Gerhard Gerber; Werner Siems; Andreas Werner, all of Berlin, Germany

[73] Assignee: Henning Berlin GmbH Chemie-und Pharmawerk, Berlin, Germany

[21] Appl. No.: 166,894

[22] Filed: Dec. 15, 1993

Related U.S. Application Data

[63] Continuation of Ser. No. 13,214, Feb. 1, 1993, abandoned, which is a continuation of Ser. No. 688,959, filed as PCT/EP89/01426, Nov. 24, 1989, abandoned.

[30] Foreign Application Priority Data

Nov. 25, 1988 [DE] Germany ................. 38 39 839.7

[51] Int. Cl.⁶ ................. A61K 9/28; A61K 9/48
[52] U.S. Cl. ............... 424/451; 424/436; 424/463; 424/474; 424/480; 424/482; 424/468; 514/258
[58] Field of Search ................. 424/457, 463, 424/490, 494, 468, 474, 480, 436; 514/258

[56] References Cited

U.S. PATENT DOCUMENTS

| 4,021,556 | 5/1977 | Springer et al. | 514/258 |
| 4,298,595 | 11/1981 | Parkinson et al. | 424/78.27 |
| 4,426,384 | 1/1984 | Wyburn-Mason | 514/258 |
| 4,871,742 | 10/1989 | Bonne et al. | 514/262 |
| 4,978,668 | 12/1990 | Babbs et al. | 514/258 |
| 5,108,758 | 4/1992 | Allwood et al. | 424/468 |
| 5,171,580 | 12/1992 | Iamartino et al. | 424/490 |
| 5,292,667 | 3/1994 | Podolsky et al. | 436/548 |
| 5,368,864 | 11/1994 | Lahr et al. | 424/489 |
| 5,378,470 | 1/1995 | Lahr et al. | 424/436 |
| 5,424,292 | 6/1995 | Pellicciari et al. | 514/19 |
| 5,430,037 | 7/1995 | Scheiffele | 514/262 |

FOREIGN PATENT DOCUMENTS

| 352686 | 10/1979 | Austria . |
| 0062000 | 10/1962 | European Pat. Off. . |
| 0261439 | 3/1988 | European Pat. Off. . |
| 975850 | 11/1964 | United Kingdom . |

*Primary Examiner*—Robert E. Sellers
*Assistant Examiner*—Amy Hulina
*Attorney, Agent, or Firm*—Jacobson, Price, Holman & Stern

[57] ABSTRACT

Chronic inflammatory intestinal diseases may be treated enterally pharmacologically active doses of said oxypurinol and or its alkali, alkaline earth, or ammonium salts.

14 Claims, No Drawings

AGENT FOR TREATING CHRONICALLY INFLAMMATORY INTESTIONAL DISEASES

This application is a continuation of U.S. application Ser. No. 08/013,214 filed Feb. 1, 1993, now abandoned; which is a continuation of U.S. application Ser. No. 07/688,959 filed as PCT/EP89/01426, Nov 24, 1989, now abandoned.

Chronic inflammatory intestinal diseases such as Morbus Crohn and colitis ulcerosa are severe diseases highly impairing the condition of affected patients, not infrequently leading to inability to work, and in certain conditions necessitating radical surgical measures with corresponding consequences.

Hitherto, a principle of causal therapy is not yet available. Treatment is effected with sulfasalazine or mesalazine, and is mostly unsatisfactory. Frequently the use of corticoids in high doses is required. According to recent findings, so-called superoxide radicals ($O_2$ radicals), and the lipid peroxidation triggered by them, play an important role in pathogenesis and sustaining of chronically inflammatory intestinal diseases. By inhibiting their formation, an effective treatment of said diseases would be given.

A substantial proportion of superoxide radicals being formed in the intestines is generated during the purine oxidation (formation of uric acid from hypoxanthine and xanthine) by action of intestinal xanthine oxidase. This can be shown inter alia by the decrease of adenine and guanine nucleotide concentrations.

For more than 20 years, allopurinol (an inhibitor of xanthine oxidase) is a standard therapeutic agent for the treatment of hyperuricaemia and gout. In the organism, it is transformed to oxypurinol to a considerable extent, which, as a major metabolite, is responsible for the prolonged action of allopurinol. Occasionally, even oxypurinol, which itself is poorly resorbable, however, has been used for gout treatment.

It has now been found that, surprisingly, oxypurinol and/or its alkali, alkaline earth, or ammonium salts upon enteral application are suitable for treating effectively chronic inflammatory intestinal diseases such as Morbus Crohn and colitis ulcerosa. For this purpose, though, it is necessary to formulate said active substances in a way as to be available in the mid and/or lower region of the small intestine. This means that oral applications are resistant to gastric juice, and thus are released only in the mid and/or lower region of the small intestine. On the other hand, it is possible to use said active substances rectally in the form of clysters.

Oxypurinol is very difficultly soluble, and therefore cannot be sufficiently resorbed, even in micronized form, to be used as an agent for the treatment of hyperuricaemia and gout. In another context, it was established that the hitherto not yet described alkali and/or alkaline earth salts of oxypurinol in amorphous or crystalline form obviously are already resorbed in the stomach and in the upper region of the small intestine, and therefore may be used for the treatment of hyperuricaemia and gout.

It is known from German Offenlegungsschrift 37 07 999 to use oxypurinol for reducing cell damages after ischaemia and prior to reperfusion, by intravenous administration of an alkali metal salt, particularly the sodium salt. However, from the examples it can be seen that not the pure sodium salt was used, but a mixture of salt and excess sodium hydroxide solution. This follows especially from the pH values of about 1 to 2% solutions, being 11.5 or 12.0. The sodium salt having been prepared by the applicant in pure and crystalline form for the first time has a pH value of 9.7 in 5% aqueous solution, and crystallizes as the monohydrate.

Thus, subject matter of the present invention are agents for enteral treatment of chronic inflammatory intestinal diseases, containing besides usual carriers and adjuvants pharmacologically active doses of oxypurinol and/or its alkali, alkaline earth, or ammonium salts, which release the active substance only in the mid and/or lower region of the small intestine, or may be used as a clysma.

Preferred subject matter of the present invention are agents, characterized in that they are suitable for oral application, resistant to gastric juice, and are released only in the mid and/or lower region of the small intestine. Preferably, agents are characterized in that they contain said oxypurinol in the form of alkali and/or alkaline earth salts in amorphous or crystalline form, and are provided as tablets or capsules resistant to gastric juice.

A preferred embodiment of the invention are agents containing said oxypurinol and/or its alkali, alkaline earth, or ammonium salts suspended or dissolved, and are provided in the form of capsules resistant to gastric juice.

Another subject matter of the invention are agents containing said oxypurinol and/or its alkali, alkaline earth, or ammonium salts in solid, suspended, or dissolved form, and provided in the form of clysters.

The agents according to the invention being applicable per os generally contain 50 to 800 mg active substance per dose unit. Clysters generally contain 50 to 500 mg active substance per dose unit.

Although, in the treatment of chronic inflammatory intestinal diseases it is crucial that said oxypurinol remains in the intestine, nevertheless agents are suitable allowing oxypurinol to dissolve in the inflamed region of the intestine, i.e., in the lower region of the small intestine or the large intestine, in order to ensure good contact to the mucosa. For this purpose, the active substance must be provided in readily soluble form, or colloidal or dispersed. With such preparations, care must be taken that the active substance is formulated resistant to gastric juice, and is released only in the mid or lower region of the small intestine. Of course, it is also possible to use such preparations per rectum in the form of clysters.

According to the invention, it is possible in addition to combine oxypurinol and/or its alkali, alkaline earth, or ammonium salts with the hitherto used agents sulfasalazine or mesalazine, use them.

Preparations being resistant to gastric juice generally have a coating, which dissolves only above a pH value of 3, preferably only in a pH range of from 5 to 7.5, and releases the active substance only in the region of the digestive tract, where correspondingly high pH values are provided. Suitable as coatings are for instance known surface coatings such as polymers of acrylic acid (Eudragite®), in particular water-dispersible forms and mixtures thereof, as well as cellulose derivatives such as hydroxypropyl methyl cellulose and derivatives thereof, namely phthalates, acetate succinates, or cellulose acetate phthalates. From said formulations the oxypurinol is released only in the lower region of the small intestine and in the large intestine, there producing an effective inhibition of xanthine oxidase, and thus preventing the formation of superoxide radicals acting as inflammatory mediators. It turned out that oxypurinol and/or its alkali, alkaline earth, or ammonium salts are suitable in the treatment of chronic inflammatory intestinal diseases both in the acute phase and in the prevention of a relapse.

With oral application, the pharmacologically effective doses generally amount to 100 to 800 mg per day, and with rectal application, 50 to 500 mg per day.

The preparation of the novel alkali and alkaline earth salts of oxypurinol in amorphous or crystalline form proceeds in a per se known manner. Since they are more readily and faster soluble as compared to micronized oxypurinol, they do provide the active substance faster and in larger quantities, but at the same time this leads to increased resorption of the active substance into the serum. This may be desirable with patients suffering from hyperuricaemia and gout. However, it is possible o limit the resorption ratio through the specific galenic formulation. Low resorption of the active substance is not impairing, since oxypurinol is well tolerated in the provided dose, and is well eliminated renally. It is crucial in the treatment of chronic inflammatory intestinal diseases that a sufficient quantity of oxypurinol is being provided within the intestine, so as to inhibit xanthine oxidase effectively, and thus preventing the formation of superoxide radicals acting as inflammatory mediators.

In addition to the agents according to the invention, it is a further subject matter of the present invention to use oxypurinol and/or its alkali, alkaline earth, or ammonium salts for the preparation of agents for the enteral treatment of chronic inflammatory intestinal diseases.

Finally, a subject matter of the invention is a method for enteral treatment of chronic inflammatory intestinal diseases by application of pharmacologically effective doses of oxypurinol and/or its alkali, alkaline earth, and/or ammonium salts.

In the following examples the various subject matters of the present invention are more fully explained.

EXAMPLE 1

Preparation of Oxypurinol Sodium 1 part by weight of pure oxypurinol is suspended with 16.5 to 17 parts by weight of deionized water. With stirring and heating up to 90° C., 30% pure sodium hydroxide solution is added from 40° C. on, each time until pH 11, and filtered hot. On rapid cooling to about 25° C., a crystal slurry is formed, which is cooled further down to 1° C. to 2° C. The crystal slurry is separated and washed several times with pure methanol, and dried at 60° C.

Yield about 80% of oxypurinol sodium.

Work-up of the mother liquor gives an additional 15%.

Properties of Oxypurinol Sodium

Empirical formula: $C_5H_3N_4O_2Na;H_2O$ MW 192.1

Said sodium salt is monosodium oxypurinol monohydrate. The salt is white and crystallizes in fine needles. In aqueous solution, it reacts alkaline, and a 5% solution has a pH value of 9.7. Its solubility is:

in water at 25° C. 15.8 g/l 0° C. 7.2 g/l ;

in methanol/water (3:1 by vol.) at 25° C. about 2.0 g/l .

The salt is stable in air and endures drying temperatures up to about 70° C. From its hot solution, oxypurinol can be precipitated almost quantitatively with diluted hydrochloric acid (10%).

EXAMPLE 2

Preparation of Oxypurinol Sodium

In a mixture of 25 l of pure methanol and 2.6 l of deionized water, 1 kg of dry oxypurinol is suspended, and within 1 h a solution of 525 g NaOH, pure, and 4.725 l of deionized water is added with stirring. A crystal slurry is formed, which is separated after a 3 hour period of stirring (suction filter or pressure filter), washed with 10 l of pure methanol in portions, and dried at 60° C.

Yield about 95% of oxypurinol sodium.

EXAMPLE 3

Preparation of Oxypurinol Potassium

As in example 2, oxypurinol is suspended in 90% methanol, and accordingly reacted with KOH.

Yield about 85% of oxypurinol potassium.

EXAMPLE 4

Preparation of Oxypurinol Magnesium

The aqueous suspension of pure oxypurinol (2 moles) with 1 mole magnesium chloride is reacted with an excess of strongly basic ion exchange resin (e.g. DOWEX 1 SBR or Amberlite IRA 400 ) at about 60° C. with stirring, the resin is separated, and after evaporation the magnesium salt is precipitated with isopropanol. The magnesium salt is obtained in amorphous form.

EXAMPLE 5

Preparation of Enteric-Coated Oxypurinol Sodium Tablets 113.7 g of oxypurinol sodium according to example 1 are mixed dryly with 30 g of microcrystalline cellulose, 6.0 g of cross-linked polyvinylpyrrolidone, and 2.1 g of polyvinylpyrrolidone (average molecular weight about 25,000 ), wetted with water, the resulting granulate is dried and subsequently mixed with 1.2 g of magnesium stearate. From the granulate, tablets are pressed having a diameter of 3 mm and a height of 1.6 mm, which are pre-isolated with hydroxypropyl methyl cellulose and subsequently coated with a coating of hydroxypropylene methyl cellulose acetate succinate being dispersible in water and resistant to gastric juice. From a pH value of 7.0 on, the film dissolves rapidly and allows for prompt liberation of the active substance from the preparation.

The film tablets may be filled into capsules of solid gelatin. It is also possible to fill the granulate into capsules of solid gelatin, and provide the final capsules with a coating being resistant to gastric juice.

EXAMPLE 6

Preparation of Enteric-Coated Oxypurinol Sodium Tablets

From a tablet granulate according to example 5, tablets are pressed having a weight of 336 mg and a content of 250 mg of oxypurinol sodium. Naturally, tablets may be prepared from said granulate, which have a lower or higher dosage. After pre-isolation according to example 5, they are coated with a coating of hydroxypropylene methyl cellulose acetate succinate being dispersible in water and resistant to gastric juice.

From a pH value of 7.0 on, the film dissolves rapidly and allows for prompt liberation of the active substance from the presentation.

EXAMPLE 7

Preparation of Enteric-Coated Oxypurinol Sodium Tablets With Delayed Release of Active Substance From a tablet granulate according to example 5, tablets are pressed having a diameter of 2 mm and a height of 1.2 mm, and are provided in a per se known manner with a film of Eudragite®, in particular with forms and mixtures thereof being dispersible in water, or a similar film varnish effecting a delayed release of active substance during the intestinal passage. Subsequently, there is applied a film layer being resistant to gastric juice according to example 5. In order to formulate the required dose forms, the minitablets are filled into capsules of solid gelatin.

EXAMPLE 8

Preparation of Enteric-Coated Oxypurinol Tablets With Delayed Release of Active Substance 152.1 g of oxypurinol are micronized in an air-swept mill and processed to solid gelatin capsules according to example 7.

EXAMPLE 9

Preparation of Enteric-Coated Oxypurinol Potassium Tablets With Delayed Release of Active Substance A granulate according to example 5 is prepared using oxypurinol potassium instead of the sodium salt. Tablets an be pressed therefrom having doses suitable for therapy, preferably 60 to 340 mg per tablet. The tablets are provided with a coating effecting a delayed liberation in the intestine and being resistant to gastric juice.

EXAMPLE 10

Preparation of Oxypurinol Sodium Clysters

Micronized oxypurinol sodium in a 0.1 to 3% carboxymethyl cellulose sodium solution, with addition of usual preserving agents such as parahydroxybenzoic acid esters and small amounts of defoamers, preferably silicone defoamers, in a concentration being optionally adjusted, preferably of from 50 to 500 mg per 100 ml volume, is suspended and filled into clyster flasks.

EXAMPLE 11

Preparation of Oxypurinol Clysters

Micronized oxypurinol sodium is used for the preparation of clysters according to example 10.

EXAMPLE 12

Histologic Determination of the Antiphlogistic Effect of Oxypurinol Sodium on Colitis of Rats Triggered by TNB (Trinitrobenzenesulfonic Acid)

In 10 rats (weight: 200–250 g) a colitis was triggered by rectal instillation of 25 mg of TNB (in 0.25 ml 30% ethanolic solution). A group of 10 animals having been treated in the same manner received from the 3rd–21st day after TNB administration 5 mg of oxypurinol Na having been dissolved in 0.5 ml of glucose solution per os via probang in 8 hour intervals. Another group of 10 animals received only 0.25 ml of said 30% ethanol solution via rectal instillation, and another 10 animals served as control.

The intestine (rectum) of the animals treated with TNB showed a chronically relapsing colitis of degree II -III. In some of the animals, there were observed incomplete erosions, particularly in the areas of the surface epithelium situated above the lymphatic follicles, very dense infiltrates in the submucosa, and plenty of perivascular mast cells within the surrounding fatty tissue. The animals treated with TNB and oxypurinol Na showed inflammatory symptoms being clearly less distinctive (degree I): slight increase of lymphocytes and mast cells and a mild oedema.

EXAMPLE 13

Biochemical Determination of the Antiphlogistic Effect of Oxypurinol Sodium on Colitis of Rats Triggered by TNB Trinitrobenzenesulfonic Acid)

Intestine samples from the animal groups characterized in example 12 were examined on the 21st day for content of purine nucleotides and lipid peroxidation products (thiobarbituric acid-reactive substances: TBA-RS). The contents of adenine nucleotides and guanine nucleotides from the TNB oxypurinol group, ethanol group, and control group did not differ significantly, whereas in the TNB group, ATP had decreased to 61%, GTP to 40%, and the sum of adenine nucleotides to 71%.

The increased concentration of TBA-RS after TNB application is lowered to 46% by addition of oxypurinol Na, and is thus even lower than the control values. Therefore, oxypurinol Na prevents the decrease of adenine nucleotides and guanine nucleotides triggered by TNB, and the enhanced lipid peroxidation.

We claim:

1. A pharmaceutical composition useful for the treatment of a chronic inflammatory intestinal disease comprising an effective amount of oxypurinol, an alkali, alkaline earth, or ammonium salt of oxypurinol, or a mixture thereof, together with (a) a material which effects release of the oxypurinol or its salt only in the mid to lower region of the small intestine, in the form of an enteric coated tablet or capsule, or (b) which is in the form of clysters.

2. The composition as claimed in claim 1, wherein the enteric coating is selected from the group consisting of an acrylic acid polymer, hydroxypropyl methyl cellulose, a phthalate derivative of hydroxypropyl methyl cellulose, an acetate succinate derivative of hydroxypropyl methyl cellulose, and a cellulose acetate phthalate derivative of hydroxypropyl methyl cellulose.

3. The composition as claimed in claim 1 which contains 50 to 800 mg per dose unit of oxypurinol, an alkali, alkaline earth, or ammonium salt of oxypurinol, or a mixture thereof.

4. The composition as claimed in claim 1 which contains 50 to 500 mg per dose unit of oxypurinol, an alkali, alkaline earth, or ammonium salt of oxypurinol, or a mixture thereof.

5. The composition as claimed in claim 1 which further comprises sulfasalazine or mesalazine.

6. A method for enteral treatment of chronic inflammatory intestinal disease, which comprises administering to a patient in need thereof a composition comprising an effective amount of oxypurinol, an alkali, alkaline earth, or ammonium salt of oxypurinol, or a mixture thereof together with (a) a material which effects release of the oxypurinol or its salt only in the mid to lower region of the small intestine, in the form of an enteric coated tablet or capsule, or (b) which is in the form of clysters.

7. The method as claimed in claim 1, wherein the enteric coating is selected from the group consisting of an acrylic acid polymer, hydroxypropyl methyl cellulose, a phthalate derivative of hydroxypropyl methyl cellulose, an acetate succinate derivative of hydroxypropyl methyl cellulose, and a cellulose acetate phthalate derivative of hydroxypropyl methyl cellulose.

8. The method as claimed in claim 6 wherein the composition contains 50 to 800 mg per dose unit of oxypurinol, an alkali, alkaline earth, or ammonium salt of oxypurinol, or a mixture thereof.

9. The method as claimed in claim 6 wherein the composition contains 50 to 500 mg per dose unit of oxypurinol, an alkali, alkaline earth, or ammonium salt of oxypurinol, or a mixture thereof.

10. The method as claimed in claim 6 wherein the composition further comprises sulfasalazine or mesalazine.

11. The composition as claimed in claim 1, which is in the form of clysters.

12. The composition as claimed in claim 1, which is in the form of an enteric coated tablet or capsule.

13. The method as claimed in claim 6, wherein the composition is in the form of clysters.

14. The method as claimed in claim 6, wherein the composition is in the form an enteric coated tablet or capsule.

* * * * *